US008277819B2

(12) United States Patent
Jiang et al.

(10) Patent No.: US 8,277,819 B2
(45) Date of Patent: Oct. 2, 2012

(54) NOROVIRUS PARTICLE FOR USE AS AN ANTIVIRAL OR VACCINE

(75) Inventors: Xi Jiang, Cincinnati, OH (US); Ming Tan, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 817 days.

(21) Appl. No.: 11/917,862

(22) PCT Filed: Jun. 15, 2006

(86) PCT No.: PCT/US2006/023407
§ 371 (c)(1),
(2), (4) Date: Dec. 17, 2007

(87) PCT Pub. No.: WO2006/138514
PCT Pub. Date: Dec. 28, 2006

(65) Prior Publication Data
US 2009/0280139 A1    Nov. 12, 2009

Related U.S. Application Data

(60) Provisional application No. 60/691,172, filed on Jun. 16, 2005.

(51) Int. Cl.
*A61K 39/125*     (2006.01)

(52) U.S. Cl. ................. 424/216.1; 424/196.11; 424/9.2; 435/5

(58) Field of Classification Search ........................ None
See application file for complete search history.

(56) References Cited

U.S. PATENT DOCUMENTS

| | | | |
|---|---|---|---|
| 5,559,014 A | 9/1996 | Estes et al. | |
| 5,861,241 A | 1/1999 | Herrmann et al. | |
| 6,156,883 A | 12/2000 | Estes et al. | |
| 6,572,862 B1 | 6/2003 | Estes et al. | |
| 6,593,080 B1 | 7/2003 | Smith | |
| 2003/0129588 A1 | 7/2003 | Estes et al. | |

FOREIGN PATENT DOCUMENTS

| | | |
|---|---|---|
| WO | WO 2005/030806 A2 | 4/2005 |
| WO | WO 2005/032457 A2 | 4/2005 |

OTHER PUBLICATIONS

Centers for Disease Control and Prevention Information Page, CDC-Norovirus: Q&A, accessed online at <<http://www.cdc.gov/ncidod/dvrd/revb/gastro/norovirus-qa.htm>> on Sep. 29, 2010.*
Burton-MacLeod, J.A. et al., Evaluation and Comparison of Two Commercial Enzyme-Linked Immunosorbent Assay Kits for Detection of Antigenically Diverse Human Noroviruses in Stool Samples, Journal of Clinical Microbiology, vol. 42, No. 6, Jun. 2004, pp. 2587-2595.
Huang, P. et al., Noroviruses Bind to Human ABO, Lewis, and Secretor Histo-Blook Group Antigens: Identification of 4 Distinct Strain-Specific Patterns, The Journal of Infectious Diseases, vol. 188, Jul. 1, 2003, pp. 19-31.
Tan, M et al., The P Domain of Norovirus Capsid Protein Forms a Subviral Particle that Binds to Histro-Blood Group Antigen Receptors, Journal of Virology, vol. 79, No. 22, Nov. 2005, pp. 14017-14030.
Bertolotti-Ciarlet et al., Structural Requirements for the Assembly of Norwalk Virus-Like Particles, Journal of Virology, vol. 76, No. 8, Apr. 2002, pp. 4044-4055.
Chakravarty et al., Evolutionary Trace Residues in Noroviruses: Importance in Receptor Binding, Antigenicity, Virion Assembly, and Strain Diversity, Journal of Virology, vol. 79, No. 1, Jan. 2005, pp. 554-568.
Chen et al., Inter- and Intragenus Structural Variations in Caliciviruses and Their Functional Implications, Journal of Virology, vol. 78, No. 12, Jun. 2004, pp. 6469-6479. Published on-line May 26, 2004, mail date May 28, 2004.
Hardy et al., Specific Proteolytic Cleavage of Recombinant Norwalk Virus Capsid Protein, Journal of Virology, vol. 69, No. 3, Mar. 1995, pp. 1693-1698.
Huang et al., Norovirus and Histo-Blood Group Antigens: Demonstration of a Wide Spectrum of Strain Specificities and Classification of Two Major Binding Groups among Multiple Binding Patterns, Journal of Virology, vol. 79, No. 11, Jun. 2005, pp. 6714-6722. Published on-line May 12, 2005, mail date May 13, 2005.
Jiang et al., Expression, Self-Assembly, and Antigenicity of the Norwalk Virus Capsid Protein, Journal of Virology, vol. 66, No. 11, Nov. 1992, pp. 6527-6532.
Prasad et al., X-ray Crystallographic Structure of the Norwalk Virus Capsid, Science, vol. 286, Oct. 1999, pp. 287-290.
Tan et al., E.coli-Expressed Recombinant Norovirus Capsid Proteins Maintain Authentic Antigenicity and Receptor Binding Capability, Journal of Medical Virology, vol. 74, 2004, pp. 641-649. Published on-line Oct. 13, 2004.
Tan et al., The P Domain of Norovirus Capsid Protein Forms Dimer and Binds to Histo-Blood Group Antigen Receptors, Journal of Virology, vol. 78, No. 12, Jun. 2004, pp. 6233-6242. Published on-line May 26, 2004, mail date May 28, 2004.
Tan et al., Mutations within the P2 Domain of Norovirus Capsid Affect Binding to Human Histo-Blood Group Antigens: Evidence for a Binding Pocket, Journal of Virology, vol. 77, No. 23, Dec. 2003, pp. 12562-12571.
White et al., Attachment and Entry of Recombinant Norwalk Virus Capsids to Cultured Human and Animal Cell Lines, Journal of Virology, vol. 70, No. 10, Oct. 1996, pp. 6589-6597.
White et al., Biochemical Characterization of a Smaller Form of Recombinant Norwalk Virus Capsids Assembled in Insect Cells, Journal of Virology, vol. 71, No. 10, Oct. 1997, pp. 8066-8072.
Bereszczak et al., Structure, stability and dynamics of norovirus P domain derived protein complexes studied by native mass spectrometry, Journal of Structural Biology, Feb. 2012, vol. 177, No. 2, pp. 273-282, published online Jan. 12, 2012 (10 pages).

(Continued)

Primary Examiner — Benjamin P Blumel
(74) Attorney, Agent, or Firm — Hasse & Nesbitt LLC; Daniel F. Nesbitt

(57) ABSTRACT

Norovirus capsid protein monomers having only the P domain, and not the hinge or S domain, can assemble spontaneously into an icosahedral form herein called the P-particle. Factors affecting the formation and stability of the P-particle, as well as providing methods for diagnosing and treating Norovirus-infected individuals and creating a vaccine for prevention of Norovirus infection are presented.

18 Claims, 10 Drawing Sheets

OTHER PUBLICATIONS

Tan et al., Noroviral P particle: structure, function and applications in virus-host interaction, Virology, Dec. 5, 2008, vol. 382, No. 1, pp. 115-123, published online Oct. 16, 2008. (9 pages).

Tan et al., Norovirus P Particle, a Novel Platform for Vaccine Development and Antibody Protection, Journal of Virology, Jan. 2011, vol. 85, No. 2, pp. 753-764, published ahead of print Nov. 10, 2010. (12 pages).

Tan et al., Terminal modifications of norvirus P domain resulted in a new type of subviral particles, the small P particles, Virology, 2011, vol. 410, pp. 345-352, published online Dec. 10, 2010. (8 pages).

Tan et al. The formation of P particle increased immunogenicity of norovirus P protein, Immunology, May 2012, vol. 136, pp. 28-29. (2 pages).

* cited by examiner

Intact VA387 VLPs

Partially dissociated VA387 VLPs

Partially dissociated NV VLPs

Partially dissociated VA387 VLPs

A

▲ binding to H antigen without blocking
△ binding to H antigen with blocking
■ binding to A antigen without blocking
□ binding to A antigen with blocking
● binding to B antigen without blocking
○ binding to B antigen with blocking The VA387 P-particle blocks
Binding of NV VLP to HBGAs

B

The VA387 P dimer blocks
Binding of NV VLP to HBGAs

Fig. 5

NOROVIRUS PARTICLE FOR USE AS AN ANTIVIRAL OR VACCINE

CROSS REFERENCE TO RELATED APPLICATIONS

This is the National Stage of International Application PCT/US06/23407, with an international filing date of Jun. 15, 2006, which claims the benefit of U.S. Provisional Application Ser. No. 60/691,172, filed on Jun. 16, 2005.

GOVERNMENT RIGHTS

This invention was made with Government support by the U.S. National Institutes of Health (National Institute of Allergy and Infectious Diseases, grant RO1 AI37093-7, and National Institute of Child Health and Human Development, grant HD13021) and the Department of Defense (DoD grant PR033018). The government has certain rights in this invention.

FIELD OF THE INVENTION

The present invention relates in general to Noroviruses, and in particular to the P domain of the Norovirus capsid protein, the formation of a small particle (the P-particle) having enhanced receptor binding to human histo-blood group antigen (HBGA) receptors, to the use of the P-particle for diagnosis of Norovirus infection, and for antiviral and vaccine development.

BACKGROUND OF THE INVENTION

Norovirus (NOR), also known previously as "Norwalk-Like Virus" (NLV) or small round structured virus, is the most important viral pathogen of epidemic acute gastroenteritis that occurs in both developed and developing countries. NORs belong to the Caliciviridae family and are icosahedral, single stranded, positive-sense RNA viruses whose capsids are composed of 180 copies of a single major structural protein.

In the past, the biological characterization of human noroviruses had been hampered because the virus has failed to grow in cell cultures and no suitable animal models have been found for virus cultivation. Human stool samples obtained from outbreaks and from human volunteer studies were the only source of the virus, yet the concentration of the virus in stool is so low that virus detection with routine electron microscopy was not possible. However, the recently successful expression of NOR capsid proteins by baculoviruses (double stranded DNA viruses which infect mainly insects) in insect cells has provided a valuable alternative for studying the immunology, epidemiology and pathogenesis of noroviruses. The viral capsid proteins produced self-assemble into virus-like paricles (VLPs). These VLPs are morphologically and antigenically indistinguishable from authentic viruses found in human feces, providing a useful tool for development of immunological assays and for study of receptor-virus interaction.

The atomic structure of the recombinant NOR capsid protein indicates that it contains 180 capsid protein monomers organized into 90 dimeric capsomers that form a T=3 icosahedron. Data from cryoelectron microscopy and X-ray crystallography showed that the viral capsid protein folds into two major domains, the S domain (or the N-terminal Shell) and the P domain (the C-terminal protrusion). The S domain forms the interior shell, while the P domain builds up arch-like structures that protrude from the shell. Morphogenesis studies showed that the S domain contains elements required for assembly of the capsid, whereas intermolecular contacts between dimeric subunits of the P domain increase the stability of the capsid. The P domain is further divided into P1 and P2 domains, with the latter located at the most exterior surface of the capsid. In contrast to the S and P1 domains, the P2 domain has a high sequence variation and therefore is believed to be critical in immune recognition and receptor binding. It has been shown that isolated P domains with the hinge (but lacking the S domain) form dimers in vitro that maintain binding to HBGA receptors.

NORs recently have been found to recognize human histo-blood group antigens (HBGAs) as receptors. Among the HBGAs, the most commonly encountered blood groups are ABO (ABH) and Lewis. The biosynthetic pathways used in forming antigens in the ABH, Lewis, P, and I blood group systems are interrelated. HBGAs have been linked to infection by several bacterial and viral pathogens. This suggests that the HBGAs are a recognition target for pathogens and may facilitate entry into a cell that expresses or forms a receptor-ligand bond with the antigens. While the exact nature of such an interaction is not currently known, close association of a pathogen that would occur with antigen binding may play a role in anchoring the pathogen to the cell as an initial step in the infection process.

Human HBGAs are complex carbohydrates linked to glycoproteins or glycolipids that are present on the red blood cells and mucosal epithelial cells or as free antigens in biological fluids, such as blood, saliva, intestinal contents, and milk. These antigens are synthesized by sequential additions of monosaccharides to the antigen precursors by several glycosyltransferases that are genetically controlled and known as the ABO, Lewis, and secretor gene families.

Co-pending patent application, PCT/US2003/017247, filed Jun. 2, 2003, which is incorporated herein by reference in its entirety, relates to the discovery that norovirus strains bind to ABO and Lewis HBGAs in one of several distinct patterns. Further, it has recently been found that the recognition of HBGAs by noroviruses is strain specific, and eight distinct receptor binding patterns have been identified. More binding patterns are expected to be found, based on the diversity of noroviruses and the polymorphism of carbohydrates on host cell surface.

The prototype norovirus, the Norwalk Virus (NV) strain, represents one of these identified binding patterns that binds to BBGAs of types A and O secretors but not of non-secretors. The other known binding patterns include strain VA387 that recognize A, B and O secretors, and MOH that binds to A and B secretors. Human volunteer studies have shown the linkage of norovirus binding to HBGA with clinical infection, which demonstrated, for example, that individuals who are non-secretors were naturally resistant to NV infection following the challenge. Thus, it seems logical to expect that each of the other binding patterns has its own host ranges defined by blood types, although direct evidence for this hypothesis remains to be established. However, a recent human volunteer study using Snow Mountain Virus, a genotype II (GII of the three known genotypes) norovirus strain, did not reveal a clear correlation between infection and blood types, suggesting that factors other than HBGAs may play a role for the infection of this strain.

In light of the foregoing, it would be advantageous to provide a better understanding of the function of the P domain of the norovirus capsid and how it interacts with HBGAs. It would also be advantageous to provide a vaccine against norovirus that includes an immunogenic response to the P domain of the norovirus capsid.

SUMMARY OF THE INVENTION

A first aspect of the present invention relates to a kit for diagnosing norovirus infection in an individual comprising (a) hyperimmune or monoclonal antibodies to P-particles created by immunizing small animals with purified recombinant P-particles from a Norovirus strain; and (b) an enzyme-linked immuno assay that can detect norovirus P-particles in the individual's stool.

A second aspect of the invention relates to a method of making a kit for diagnosing norovirus infection in an individual, the method comprising the steps of (a) purifying recombinant P-particles from a Norovirus strain; (b) using the purified P-particles to immunize small animals to produce hyperimmune or monoclonal antibodies to P-particles; and (c) using the hyperimmune or monoclonal antibodies to create an enzyme-linked immuno assay that can detect norovirus P-particles in the individual's stool. The Norovirus strain is preferably VA387, MOH or NV.

A third aspect of the invention relates to a kit for diagnosing a norovirus infection in an individual, the kit comprising (a) purified recombinant P-particles from a Norovirus strain; and (b) an enzyme-linked immuno assay that can detect antibodies to the Norovirus strain in the individual's serum. The Norovirus strain is preferably VA387, MOH or NV. Use of the enzyme-linked immuno assay typically includes the steps of (1) pre-coating the purified recombinant P-particles onto a plate used in the enzyme-linked immuno assay; (2) adding the individual's serum to the plate; (3) adding anti-human immunoglobulin which is coupled to an enzyme to the plate; (4) adding a substrate to the plate which changes color when cleaved by the enzyme; and (5) determining if the substrate changes color, whereby a positive diagnosis of Norovirus infection can be made.

A fourth aspect of the invention relates to a method of diagnosing Norovirus infection in an individual, the method comprising the steps of (a) purifying recombinant P-particles from a Norovirus strain selected from the group consisting of VA387, MOH and NV; and (b) using the purified recombinant P-particles and the individual's saliva in an enzyme-linked immuno assay to determine the individual's blood type. This method can also be in the form of a kit.

A fifth aspect of the invention relates to a method of treating an infection in a mammal caused by a microbial pathogen which recognizes human histo-blood group antigens as receptors, the method comprising administering a therapeutic amount of P-particle to an infected individual. The microbial pathogens can be Norovirus, *helicobacter pylori*, *campylobacter* species, *vibrio cholera*, uropathogenic *E. coli*, *candida* species, or some other microbial pathogen. The P-particle can be a purified recombinant P-particle in the shape of an icosahedron, with the icosahedron being comprised of 24 monomer units of SEQ ID NO:2. The P-particle can also be a purified recombinant P-particle from a Norovirus strain selected from the group consisting of VA387, MOH and NV.

A sixth aspect of the invention relates to a vaccine for the prevention of Norovirus infection in humans, the vaccine comprising a therapeutic amount of a compound having increased receptor binding activity with human histo-blood group antigens in a suitable sterile, nontoxic physiological medium. The compound can be P-particle or it can be a capsid protein monomer in the form of SEQ ID NO:1, SEQ ID NO:2, a P protein, a dimer of the P protein, a pentamer of dimers of the P protein, or mixtures thereof.

A seventh aspect of the invention relates to a method of protecting humans from Norovirus diseases, the method comprising administering to a human an immunizing amount of capsid protein from the norovirus strain VA387 in a sterile, nontoxic pharmaceutically acceptable carrier.

An eighth aspect of the invention relates to a method of inducing an immune response in an individual against Norovirus, the method comprising the step of orally or parenterally administering to an individual at least one immunologically effective dose of a composition comprising an immunogen recombinantly expressed or synthesized from a cDNA comprising: a fragment of the cDNA sequence of the capsid protein of norovirus strain VA387 and a pharmaceutical carrier, wherein the dose is effective in inducing the immune response in the individual. The fragment can be SEQ ID NO: 1 or SEQ ID NO:2.

A ninth aspect of the invention relates to an isolated P-particle from a Norovirus strain. This includes an isolated, purified P-particle from a Norovirus strain which has been cysteine-modified. This aspect can also include a modified P-particle from a Norovirus strain in which a cysteine has been linked to the end of the P1 subdomain, the resulting P-particle being more stable than the original P-particle.

While the nature and advantages of the present invention will be more fully appreciated from the following drawings and detailed description, showing the contemplated novel construction, combinations and elements as herein described, and more particularly defined by the appended claims, it is understood that changes in the precise embodiments of the present invention are meant to be included within the scope of the claims, except insofar as they may be precluded by the prior art.

BRIEF DESCRIPTION OF THE DRAWINGS

FIG. 5. The P-particle of VA387 blocks the binding of NV VLP to HBGAs. A, binding curves of NV VLPs to H, A, and B antigens with or without the blockage of the VA387 P—particle (CNGRC-H/P). B, binding curves of NV VLPs to H, A, and B antigens with or without the presence of the VA387 P dimer (H/P). The monoclonal antibody 9C3 that reacts with NV but not with VA387 was used to detect the HBGA-bound NV VLP. The data were a representation of three-time repeated experiments.

DETAILED DESCRIPTION OF THE INVENTION

As used herein the term "Norovirus," "NOR", "Norwalk-like virus," or "NLV" means any virus of the Norovirus family, and includes, without limitation, the following: Norwalk Virus ("NV"), MOH, Mexico, VA 207, VA 387, 02-1419, C59, VA 115, Hawaii, Snow Mountain, Hillington, Toronto, Leeds, Amsterdam, Idaho Falls, Lordsdale, Grimsby, Southampton, Desert Shield, Birmingham, and White Rivercap.

The present invention follows from studies showing that a large amount of soluble P domain of the norovirus capsid protein exists in the stools of the norovirus-infected patients. Although the exact reason or function for this is still unknown, it's existence suggests that the isolated P domain is highly stable and may fulfill certain unknown functions. In previous studies by the inventors of the present invention on the characterization of norovirus-receptor interaction, they have found that the isolated P domain with the hinge forms a stable dimer and retains the binding function to HBGAs.

The present invention provides a small particle, known herein as the P-particle, which displays enhanced binding affinity to HBGAs. The isolated P domain, without the S domain or the hinge of the monomer capsid protein of NOR Strain VA387, can spontaneously form a T=1 icosahedral complex consisting of 24 P monomers arranged into 12 dimers. This P-particle can also bind to human intestinal Caco2 cells and reveals strong blocking of VLP binding to HBGAs. Thus, the present invention presents biochemical and biophysical evidence indicating that norovirus capsid monomers having only the P domain, and not the hinge or S domain, can assemble spontaneously into the P-particle. This has been observed in Norovirus strains VA387, MOH, and NV. The present invention also presents factors affecting the formation and stability of the P-particle, such as the addition of a cysteine residue(s) to the P domain, as well as providing a method for therapeutic treatment of norovirus infection and creating a vaccine for norovirus infection with this newly discovered P-particle.

Figure 1:
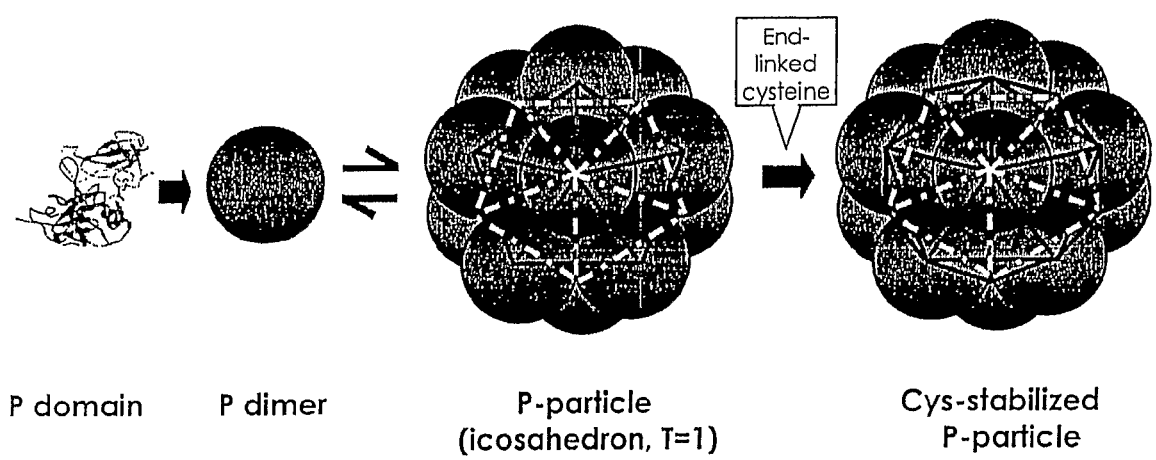
FIG. 1. A proposed model of the P-particle. Two P domain monomers form a stable global P dimer. 12 identical P dimers then assemble into a T=1 icosahedral P-particle, which exchange dynamically depending on the concentration of the P protein. The intermolecular interactions among the P domains are the original forces for the P-particle formation. End-linked cysteine(s) can stabilize the P-particle by forming intermolecular disulfide bonds.

Evidences supporting this finding include data from gel filtration, non-denatured PAGE gel, and electron microscopy. Based on the molecular weight (~830 kDa), the shape (spherical), the size (~5 μm in diameter), and the stability of the P-particle, it was predicted that the P-particle is a T=1 icosahedron built by 24 P monomers that organize into 12 identical P dimers (FIG. 1). Both 12 (P dimers) and 24 (P monomers) are perfect unit numbers for an icosahedral symmetry that occurs frequently for plant and animal viruses.

Structural study of the recombinant capsid of Grimsby virus, a strain genetically closely related with VA387, revealed a global structure of the P dimer moiety in a capsomer, suggesting that the isolated P dimer is a spherical structure that can be easily incorporated into an icosahedron.

In addition, observation of the only two peaks in the gel filtration of the P protein, each representing the P dimer and the P-particle, is consistent with the property of an icosahedron, which is stable and low energy-consuming. In fact, when 12 ping-pong balls, representing 12 P dimers, are put into a tuck net with slightly pressing and twisting, a perfect T=I icosahedron as the one predicted for the P-particle will occur (FIG. 1).

A model of the P-particle formation is illustrated in FIG. 1. The data from the atomic structure of NOR capsid indicates that there are ten (10) intermolecular interacting sites in each capsid protein, seven (7) of which are located within the P domain. Thus, it is logical to anticipate multiple intermolecular interactions among the P protein monomers, which is the original force for P dimer and the P-particle formation. Some of these interactions are used for dimerization of the P protein, while the others may be used for polymerization of the P dimers into the P-particle. In the proposed model it is hypothesized that the P monomers first form spherical P dimers as described above. Twelve (12) global P dimers then assemble into a T=1 icosahedral particle, presumably via multiple P1-P1 and P2-P2 interactions, as it is the case in a capsomer. This process can exchange or equilibrate dynamically, depending on the concentration of the P dimer.

However, when a cysteine was linked to the end of the P1 subdomain, the resulting P-particles become much more stable and much less P protein concentration-dependant than the one without the cysteine tail. DTT-treatment (dithiothreitol, used to reduce disulfide bonds quantitatively) revealed that the fused cysteine can form intermolecular disulfide bridges that strengthen the interaction among the P dimer. Although it is not clear how each P monomer is orientated in individual P dimers, each P dimer should have the same orientation in their interaction with five surrounding P dimers, forming a pentagon along the five-fold axis. As a consequence, the outer layer of the P-particle is formed by the P2 subdomain, similar to the arch structure of the norovirus capsid, while the inner layer is made by the P1 subdomain, providing support to the P2 arch. Like other icosahedral viral particles there should be a cavity inside the P-particle (See FIG. 2).

It becomes evident, based on the proposed structure of the P-particle, why the presence of the hinge inhibits the P-particle formation. The hinge provides a freedom as well as a restriction to the P domain for the icosahedral capsid formation in the presence of the S domain. In the P-particle, such freedom and restriction are no longer required because of the missing S domain. Further, the presence of the hinge becomes an extra plug interrupting the P1-P1 interaction. In contrast, the P1-linked cysteine(s) strengthen the P1-P1 interaction by disulfide bonds.

It has been shown that the N-terminal region of the capsid protein of some plant and animal viruses contain a molecular switch in controlling the conformation of the T=3 icosahedral capsid. When such a determinant was deleted in the VP60 of rabbit hemorrhagic disease virus (RHDV), an animal calicivirus, the mutant capsid protein formed a T=1 icosahedral capsid (Barcena et al., 2004). A similar mechanism has also been observed in some other T=3 plant viruses. Indeed, when the N-terminal arms of these viruses were removed, the N-terminus-less mutants assembled into T=1 particles (Cuillel et al., 1981; Erickson et al., 1985; Lokesh et al., 2002; Savithri and Ericson, 1983; Sorger et al., 1986). Thus, the formation of the T=1 particle of the isolated P domain of VA387 may be regulated by the same mechanism. However, morphogenesis studies of NOR suggest that it may use other strategies to acquire distinct conformational status, as the NOR mutant lacking the N-terminal arm is able to assemble into T=3 capsid (Bertotti-$C_1$-arlet et al., 2002). In fact, NV Tell and T=3 particle formation occurs spontaneously when the full-length capsid protein was expressed in insect cells (White et al., 1997). This indicated that other factors, such as charge configuration of the capsid protein, may further regulate the subunit interaction and the mode of the Tell versus T=3 assembly in NV. Further experiments are required to clarify these issues.

It has been noted that large amounts of P protein—i.e. soluble P domain without the S domain and the hinge—exist in the stools of norovirus-infected patients (Greenberg et al., 1981; Hardy et al., 1995). This observation indicates that the isolated P protein exists in vivo, which raises a question for the potential function of the isolated P protein in vivo. One possibility is that this P protein may serve as a viral decoy to allow the virions to escape the host immune protection. Previous studies have shown that the P protein in vivo is a result of specific protease digestion at the end of the hinge (Hardy et al., 1995). This suggests that the P protein remains folded in some structural form such that the other 16 potential trypsin cleavage sites, present in the linear sequence, are not exposed. It was thus interesting to determine if the P-particle also occurs in vivo. To explore this issue, the stool extract from norovirus-infected patients were separated by gel filtration. Enzyme-immune assays (EIAs) of the fractions revealed two absorbent peaks at positions around the P-particles and the P dimers, implying that P-particles exist in vivo.

While further experimentation is needed to explore the function of the P-particle and the P protein in vivo, the present invention concerns the formation of the P-particle in vitro for use in the diagnosis of Norovirus infection, as well as for the therapeutic treatment and the development of a vaccine for Norovirus using the P-particle. Indeed, recombinant DNA techniques have provided the ability to create recombinant P-particles from the VA387 strain of Norovirus, as well as similar P-particles from strains MOH and NV. For diagnostic purposes, P-particles can be used to immunize small animals to produce hyperimmune or monoclonal antibodies, which can then be used to develop an enzyme-linked immuno assay ("ELISA" or "EIA") for detection noroviruses in stool. P-particles also can be used as antigen to coat the plate in an EIA to detect antibodies of patients for diagnosis. In this procedure, P-particle antigens are pre-coated onto an ELISA plate, then patient serum, which are believed to contain antibodies against the P-particles, is added. If the patient does have Norovirus infection, then this serum will contain antibodies to P-particles, and those antibodies will bind to the P-particle antigens on the plate. Anti-human immunoglobulin, coupled to an enzyme, is then added as a second antibody which binds to the patient's human antibodies. Chromogen, or some other substrate which changes color when cleaved by the enzyme which is attached to the second antibody, is then added, and if the chromogen changes color then the positive diagnosis of NOR infection can be made.

Similarly, P-particles may be used to determine blood types based on EIA testing of saliva samples from humans. This is significant since current determination of Lewis and secretor blood types depends upon the creation of expensive monoclonal antibodies. Finally, norovirus P-particles may be used as therapeutics for other microbial pathogens that also recognize human HBGA as receptors, such as *helicobacter pylori, campylobacter, cholera*, uropathogenic *E. coli, candida*, etc.

Another interesting observation regarding the P-particle is the significant enhancement of binding affinity to HBGAs by the P-particles compared with that of the previously-described P dimers. The increased receptor binding sites of the P-particle compared with that of the P dimers could be a major factor in the creation of a vaccine against Norovirus. The even higher binding sensitivity of the P-particle than that of the VLP (Table 2) may be due to the increased binding affinity of P-particles than that of the VLPs (Mr=10.4 mDa) as there exists roughly about 12-fold more of the P-particles than VLPs in a given amount of proteins. In other words, the P-particles have a higher ratio of binding-site per unit mass. However, these findings cannot explain why the binding enhancement of the P-particle of VA387 was significant in regards to binding of blood types A and B compared with that to the type H antigens (Table 2). One interpretation is that the folding or conformation of the binding interface of the P-particle differs slightly from that of VLP, and this difference affected the binding to the H but not the A/B epitopes. This hypothesis is supported by a proposed model of norovirus-receptor interaction, in which two binding sites, one each for the H and A/B epitopes, are present on the binding interface of the capsid (Huang et al., 2005, in press). A further possibility is that the conformation of the binding interface is optimized during the formation of the P-particle and/or VLP. This speculation supports the observation of binding affinity changes between the VLP and its dissociated products (FIG. 3) and explains why the P-particle, but not P dimer, blocked the binding of the VLP to HBGA (FIG. 5).

The fact that the P-particle binds strongly to the human enterocyte Caco-2 (FIG. 4), and that the P-particle of VA387 (a GII strain) cross blocked the binding of NV VLP (a GI strain) to the A and H antigens (FIG. 5) suggests that large amounts of the P-particle could be used to treat norovirus infection. The easy production of the cysteine-stabilized P-particle and the survival of the P protein through the intestinal tract make this strategy more attractive. In addition, the P-particle may serve as a vaccine for a long-term protection following the treatment. In a separate study we have shown that administration of VA387 P protein to mice intranasally produced specific antibody that can block the binding of VA387 to HBGAs (unpublished data).

Figure 3:
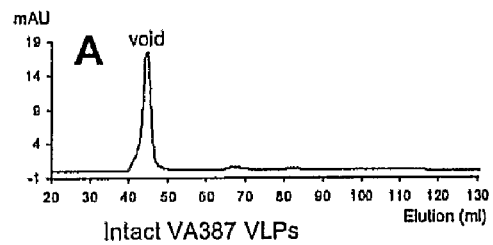
FIG. 3. The binding capability of the icosahedral VLP is higher than that of its dissociated product. A, gel filtration chromatograph of intact VA387 VLPs in 1×PBS show a single peak in the void volume. B to D, gel filtrations of partially dissociated VLPs of VA387 (B and D, left panels) and of NV (C, left panel) by 50 mM Tris, pH 9 (B and C) or 50 mM Tris containing 30% sucrose (pH 9, D), showing peaks representing the intact capsid (void), the potential pentamer of dimer (~440 kDa), capsid protein dimer (10 kDa), and degraded product (<10 kDa), respectively. For each gel filtration the peak fractions were collected and adjusted to the same concentration according to the UV reading, then was used for binding assay to A type saliva based on a 3-folds series dilution (right panel). Striped column is the binding of intact VLP while the empty column is the binding of the dissociated intermediate. Data were average of a triplicate.
Figure 3:
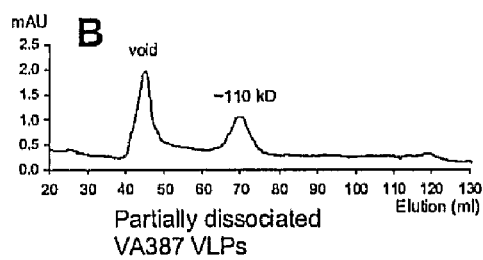
Figure 3:
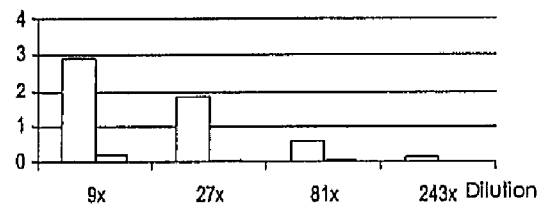
Figure 3:
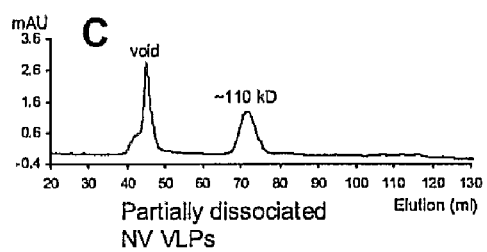
Figure 3:
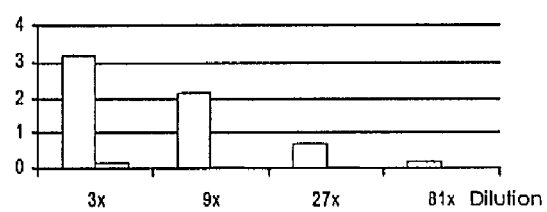
Figure 3:
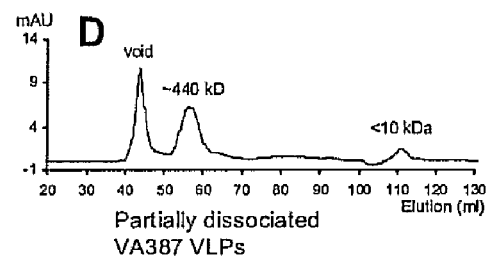
Figure 3:
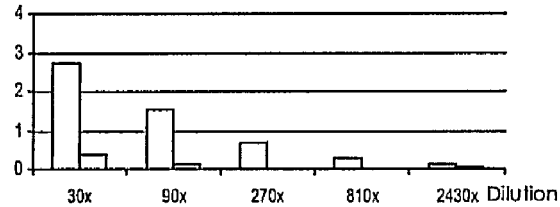

Using two different buffer conditions, we were able to dissociate the norovirus VLPs into two types of intermediates that may be equivalent to (1) a capsid protein dimer (~116 kDa); and (2) a pentamer of dimers (~580 kDa), respectively (see FIG. 3). Based on the crystal structure of NV capsid, a capsid assembly pathway has previously been proposed in which the capsid protein monomers first dimerize, and then polymerize into a pentamer of dimers, which further assemble into an icosahedral capsid. The data presented herein are the first experimental evidence supporting this proposed assembly model.

EXAMPLES

Materials and Methods

Construction of various norovirus mutants of VA387 and NV used in this invention were done by cloning the full-length or partial capsid protein-encoding genes into the pFastBac (Bac-to-Bac Baculovirus Expression System, Invitrogen, Carlsbad, Calif.) for expression in baculovirus, or into the pGEX-4T-1 (GST Gene fusion system, Aniersham Biosciences, Piscataway, N.J.) for expression in bacteria. All mutants with Nor C-terminal-linked short peptides were prepared using primers with the peptide-encoding sequences. The mutant of VA387 with TMA mutation was constructed using the QuickChange site-directed mutagenesis kit (Stratagene, La Jolla, Calif.). The mutants CNGRCTTDC-H/P and CVQPCNGRC—H/P were made from the construct CNGRC—H/P by site-directed mutagenesis. The construct for expressing CNGRC-MBP was made by amplifying the MBP-encoding sequence from the plasmid pMALc2 (NEB, Hercules, Calif.) using primer containing CNGRC-encoding sequence. All mutant sites and cloning conjunctions of the constructs were confirmed by sequencing. Table 1 lists all the primers used in this invention.

Experiment #1

Expression and Purification of Norovirus VLPs

The capsid proteins of NV and VA387, representing genogroup GI and GII, respectively, of norovirus, were expressed in insect cell *Spodoptera frugiperda* (sf9) using the Bac-to-Bac baculovirus expression system (Invitrogen, Carlsbad, Calif.). The Bac-to-Bac baculovirus system (Invitrogen) provides a rapid way for the generation of recombinant baculoviruses. It is based on site-specific transposition of an expression cassette into a baculovirus shuttle vector (bacmid). Briefly, the cDNA sequence of the open reading frames 2 and 3 were cloned into pFastBac donor plasmid and transposed into the bacmid. Sf9 insect cells were then infected with the recombinant bacmid containing the capsid protein-encoding gene. The VLPs from the infected insect cells were purified by a sucrose gradient containing 5 sucrose concentrations from 10% to 50%. The purified VLPs were stored at minus 70 degrees Celsius in 1×PBS, pH 7.4.

Experiment #2

Expression and Purification of Recombinant Capsid Proteins in *E. Coli*

After sequence confirmation, the constructs were expressed in *E. Coli* strain BL21 at room temperature over night with an induction of 0.5 mM IPTG. Purification of the recombinant proteins from bacteria was performed using Glutathione Sepharose 4 Fast Flow (Amersham Bioscience, Piscataway, N.J.) according to the manufacturer's; instruction. The GST-capsid protein fusion was eluted by glutathione (Amersham Bioscience, Piscataway, N.J.) and the capsid proteins were released from GST by thrombin (Amersham Bioscience, Piscataway, N.J.) cleavage at room temperature for 16 hours. Further purification was conducted by gel filtration using a size-exclusion column (see below). Protein concentrations were measured spectroscopically, or by SDS quantitative PAGE gels, depending on the purity of the proteins.

Gel filtration. To further purify the capsid proteins and to measure the molecular weight of the resulting proteins of the P domain mutants, the affinity column-purified P proteins were loaded on the sized-exclusion column Superdex 200 (Amersham Bioscience, Piscataway, N.J.) powered by an AKTA FPLC System (model 920, Amersham Bioscience, Piscataway, N.J.). The protein of each peak was analyzed by SDS-PAGE gel or/and Western analysis. If the starting protein was not clean enough to have a good chromatograph, the P proteins from a previous gel filtration were pooled and reloaded for a second run of gel filtration. The molecular weight of the corresponding eluted fraction was calibrated by the Gel Filtration Calibration kit (Amersham Bioscience, Piscataway, N.J.). In this invention the gel filtrations were run using 1×PBS, pH 7.4, except otherwise indicated.

Non-denatured and non-reduced PAGE. To visualize the P-particles on a PAGE gel, the P protein was loaded on a polyacrylamide gel without SDS using a loading buffer without reduced reagent (DTT or Beta-mercaptoethanol). The samples were loaded directly onto the gel without boiling. BSA and the P dimer were loaded in the same gel as molecular weight control.

Experiment #3

Assay of Capsid Proteins Binding to HBGAs

The binding capabilities of both the wild type and mutated capsid proteins to HBGAs were measured by saliva binding enzyme immune assays. In most of the cases, synthetic oligosaccharides (Glycorex B, Lund, Sweden), were used as control to make sure that it was the HBGAs, and not other components in the saliva, which reacted with the capsid proteins.

Determination of the binding sensitivity of the capsid protein. The recombinant capsid proteins from different sources were diluted to 1 mg/ml as starting stocks. The proteins were then diluted in 3-fold series in a 96-well plate that was coated with HBGAs. A standard HBGA-binding assay was then performed. The binding sensitivities of the capsid proteins were determined by the minimum protein concentrations in a well that produced an $OD_{450}$ of $\geqq 0.1$. Baculovirus-expressed VLPs of VA387 were used as standards in each plate to calibrate the possible variation among individual plates. Since the P domain mutants are about a half of the molecular weight of the full-length capsid protein, all full-length proteins were diluted double concentrated as those of the P domain mutants to have a similar molar concentration.

Experiment #4

Blocking Assay

To measure the blocking effects of the P-particle, P dimer, and VLPs of VA387 on bindings of NV VLP to HBGAs, the well-characterized saliva with blood type of 0, A, B, and nonsecretor (Huang et al., 2003) were coated on a microplate. The P-particle, P dimer, or VLP of VA387 at different concentrations was incubated for 15 minutes prior to the incubation with NV VLP. Detection of the bound NV VLP was performed using the monoclonal antibody 9C3 that reacts with NV VLP but not with the capsid protein of VA387.

Partial dissociation of VLPs. To compare the binding sensitivities of VLPs and its dissociated products, the VLPs were partially dissociated by a treatment of 50 mM Tris, pH 9. The VLPs stored in 1×PBS (pH 7.4) and/or sucrose were dialyzed against 50 mM Tris (pH 9) for 3 to 6 hours at room temperature. Alternatively, the VLPs stored in water containing 30% sucrose were treated by adding 1 M Tris (pH 9) to an end-concentration of 50 mM and then incubated at 4° C. for 3 to 6 hours. The treated VLPs were then loaded onto a gel filtration column running in the same buffer condition. Peak fractions representing the intact VLP and the capsid protein dimer were adjudged to the same concentration according to the UW reading using a Centricon (Millipore, Danvers, Mass.) for binding assay.

Electron microscopy. To observe the morphology of the P-particle, the gel filtration purified P-particle was prepared for EM specimens as described by Bertolotti-ciarlet et al. (2003) using 1% ammonium molybdate as negative staining solution. Specimens were examined in an EM10 C2 (Zeiss, Germany) under 80 kV at primary magnification of 80,000× or 100,000×.

Mass spectrometry. The molecular weights of the P domain monomer and dimer were determined by electrospray ionization-mass spectrometry (ESI-MS) and by matrix-assisted laser desorption/ionization-mass spectrometry (MALDI-MS) performed by the core facility at the University of Cincinnati, Ohio. For ESI the P proteins were diluted in 50% Acetonitrile/water, 0.1% formic acid buffer, then analyzed through a Micromass Q-TOF II mass spectrometer (Waters Corporation Milford, Mass.). Sample was directly infused through the instrument using a syringe pump. MALDI was performed through a standard protein analysis protocol using Sinapinic acid as a matrix. The MALDI instrument used was a Bruker Daltonics Reflex IV (Billerica, Mass.).

Experiment #5

Caco-2 Cells and Fluorescence Microscopy

Caco-2 cell, a cell line from a human colon carcinoma, which has been shown to express HBGAs after differentiation, was used to test the interaction with the P proteins. The cells were cultivated and the culture was considered to be at least partially differentiated 7 to 14 days post confluency. The P dimer (H/P) and the P articles (CNGRC—HP) and a binding defecting mutant (PC-5) were labeled by biotin using the EZ-link biotinylation kit (Pierce, Rockford, Ill.). The labeled proteins were incubated with the partially differentiated cells in a 24-well plate at indicated concentration for 2 h at 37° C. After 5 times wash with HBSS with Mg++ and Ca++ (Cambrex. Bio Science, Walkersville, Md.), 300 microliter-diluted the FITC-Striptavidin (1:200, Pierce, Rockford, Ill.) was incubated with the cells for 60 min at 37° C. After washed 5 times with HBSS, cells were observed using a fluorescence microscope (Zeiss Axiovert S100, Germany) equipped with a SPOT digital camera (Diagnostic Instruments, Inc.).

Results

Figure 6:
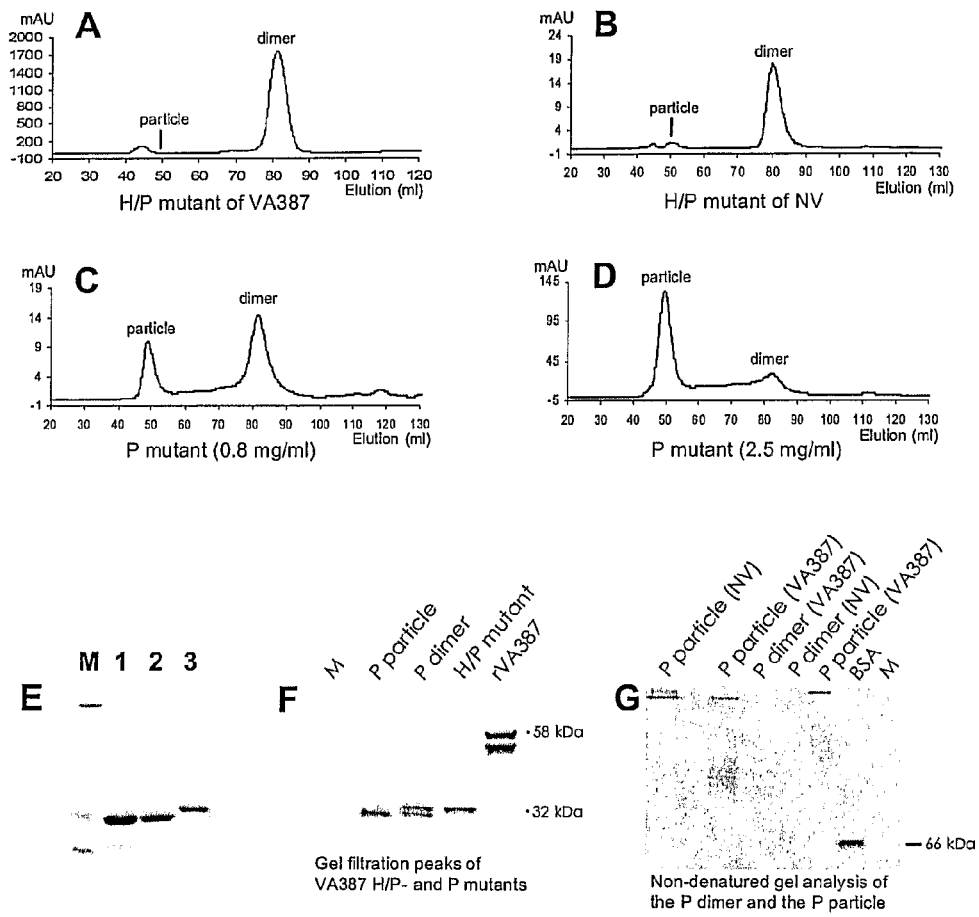
FIG. 6. The isolated P domain without the hinge forms P-particles. A to D, chromatographs of gel filtrations of the HIP mutants (A and B) and the P mutants (C and D) of strains VA387 (A, C and D) and NV (B), indicating the peaks of the P dimer and the P-particle. The minor peaks in the void volume (~45 ml) were some unknown protein aggregates. The gel filtration column was calibrated by the calibration kit (Amersham Biosciences): 2,000 kDa, 44.3 ml (void); 669 kDa, 50.1 ml; 440 kDa, 56.2 ml; 232 kDa, 65.7 ml; 146 kDa, 70.8 ml; 67 kDa, 76.7 ml; 47 kDa, 82.7 ml; 25 kDa, 92.9 ml; 13.7 kDa, 97.3 ml. E, SDS-PAGE gel stained with brilliant blue (G250) to show P proteins of the P mutants purified by affinity column (lane 1) and by anion-exchange chromatography (lane 2), as well as the P protein of CNGRC-H/P mutant purified by affinity column, followed by anion-exchange chromatography (lane 3). F, Western analysis of the peaks of gel filtrations representing the P dimer and the P-particle of VA387 using hyperimmune sera against the VLPs of VA387. G, non-denatured PAGE gel stained with Brilliant Blue (G250) to visualize the P-particles as bands with high molecular weight. H and I, mass spectrometry analysis to measure the molecular weight of the P dimer (P mutant) by electro, spray mass spectrometry (H) and by MALDI-mass spectrometry (I).

The isolated P domain without the hinge forms a complex of dimers. It has been reported previously that the isolated P domains with the hinge region (H/P mutant) of noroviruses form a dimer that binds to HBGAs. In the present invention, the P domain without the hinge (P mutant) of V A387 forms a special complex of dimers (the P-particle, FIG. 6C to E). Gel filtration analysis using a Superdex 200 (Amersham, Piscataway, NJ) showed that this complex was eluted at the same time as thyroglobilin (690 kDa, FIG. 6C and D), which is equivocal to 12 P dimers that was eluted at a time equals to 55 kDa (FIG. 6A and B). Non-denatured PAGE gel electrophoresis confirmed the presence of the P-particle since a single major protein band with a high molecular weight was observed (FIG. 6G). There is no major contaminated protein in the affinity column-purified P-particle base on the PAGE analysis and the P-particle can be purified to nearly homogeneity by anion exchange and gel filtration (data not shown). The fact that only a single peak of the P-particle and no intermediate product was seen in the gel filtration (FIG. 6C and D) suggests that the estimated 12 P-dimers must be arranged in a low energy-consuming order in the particle. The formation of the P-particle is concentration dependent, as ~65% of the VA387 P protein exists as dimers at a concentration of 0.8 mg/ml, whereas >95% of the P protein formed the P-particle at 2.5 mg/ml (FIG. 6C and D). To accurately measure the molecular weights of the P dimer and the P-particle, analytic mass spectrometry was performed. Both electro spray (FIG. 6H) and MALDI (FIG. 6I) mass spectrometry revealed a mass of P dimer as ~69 kDa. Accordingly, the estimated molecule weight of the P-particle (12 dimers) is ~830 kDa.

An end-linked cysteine residue promotes the P-particle formation. The fact that the P mutant, but not the H/P mutant, forms P-particle indicates that the hinge inhibits P-particle formation. In separate studies we have observed that the addition of small peptides to the ends of the P domain greatly affected the receptor binding capability of the P protein (Table 2). Since the complex formation also affected the receptor binding of the P protein (see result below), we tested the effects of these peptides on the formation of the P-particle. The first peptide tested was the CNGRC motif, a ligand of CD 13 (aminopeptidase) found in tumor blood vessels (Pasqualini et al., 2000, Cancer Research 60:722). Addition of this motif to either N- or C-terminus of the H/P mutant resulted in nearly exclusive formation of the P-particle (FIGS. 7D and E), indicating that CNGRC promoted the P-particle formation.

Figure 7:
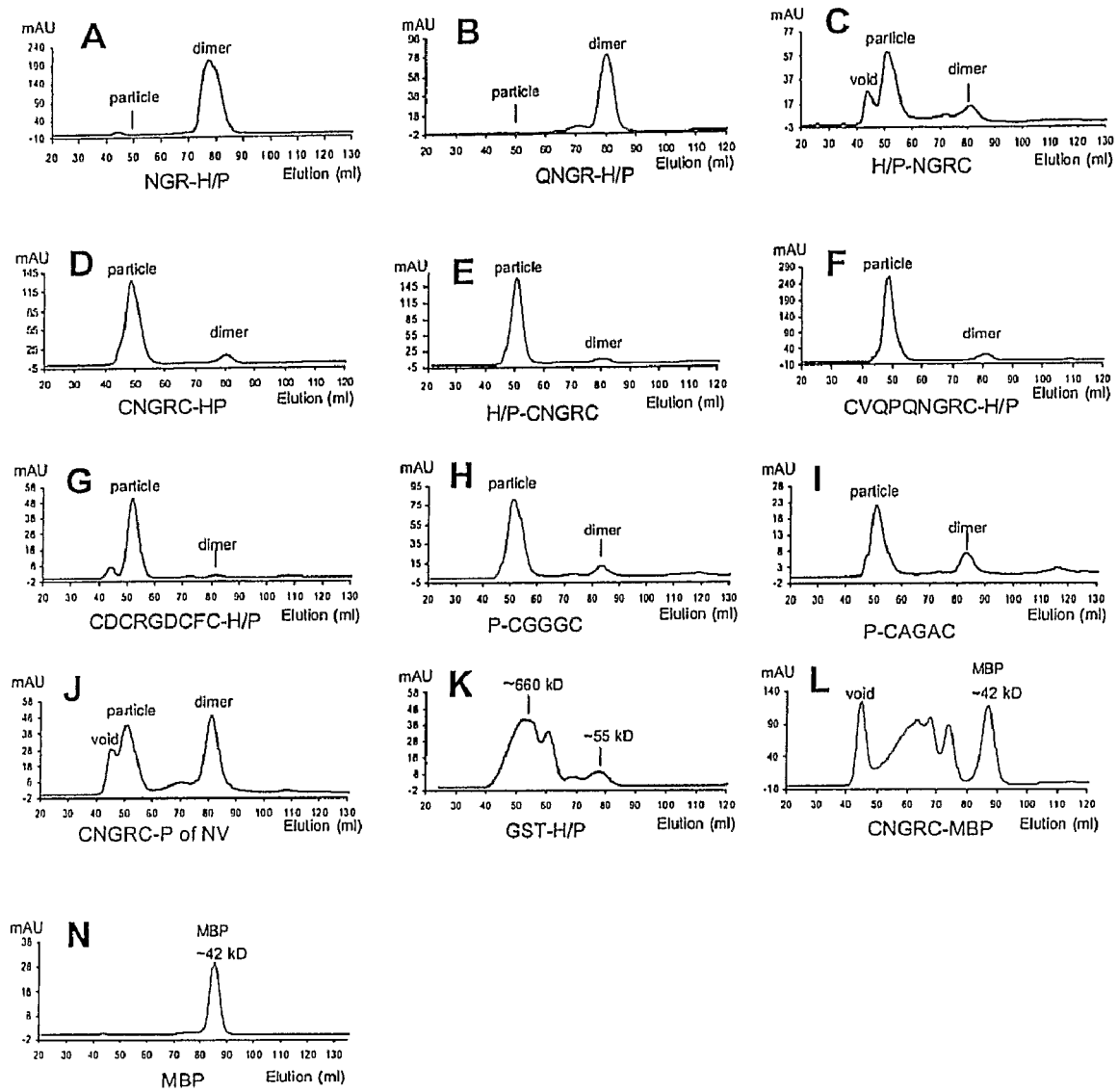
FIG. 7. An end-linked cysteine promotes the P-particle formation. A and B, H/P mutants with an N-terminus-fused short peptide without cysteine formed only P dimer. C to J, P or H/P mutants with end-linked cysteine(s) formed P-particle. The minor peaks in void volume (~45 ml) were some unknown protein aggregates. K and L, negative controls to demonstrate that the H/P mutant with GST (K) and the maltose-binding protein (MBP, Panel N) with the end-fused cysteines (L) did not form P-particle-like complexes. The gel filtration column was calibrated by the calibration kit (Amersham Biosciences): 2,000 kDa, 44.3 ml; 669 kDa, 50.1 ml; 440 kDa, 56.2 ml; 232 kDa, 65.7 ml; 146 kDa, 70.8 ml; 67 kDa, 76.7 ml; 47 kDa, 82.7 ml; 25 kDa, 92.9 ml; 13.7 kDa, 97.3 ml.

To further determine the mechanism of the P-particle formation, a panel of oligopeptides with variable sequences and different numbers of cysteine residues were tested (FIG. 7 and Table 2). When the $NGR^X$ or QNGR motifs without cysteine were fused to the N-terminus of the H/P mutants of VA387, the resulting P proteins formed dimer only (FIGS. 7A and B, compare to FIGS. 7D and E). On the other hand, when the peptides containing cysteines but not the NGR motif were linked to the C-terminus of the H/P or P mutants, the resulting P protein mainly formed complexes (FIGS. 7H and I), indicating that the cysteine, but not the NGR motif, was important for the P-particle formation. A single cysteine residue seems sufficient for the promotion of the P-particle formation, as more cysteines only resulted in slight increase of the particle formation (compare FIG. 7C with D, E, F, and G). This particle formation is P domain specific, as fusion of the CNGRC to the C-terminus of the maltose-binding protein (MBP, 42 kDa FIG. 7N) resulted in only aggregates of protein with variable sizes (FIGS. 7L). Moreover, addition of the GST tag to the H/P mutant did not result in the P-particle formation (FIG. 7K). To examine if similar effect also occurs in a GI strain, CNGRC was fused to the H/P mutant of NV, which also promotes the P-particle formation (compare FIG. 6B with FIG. 7J), although the efficiency was lower than that of VA387. These data demonstrated that an end-linked cysteine residue promotes the P-particle formation of GI and GII strains.

Figure 8:
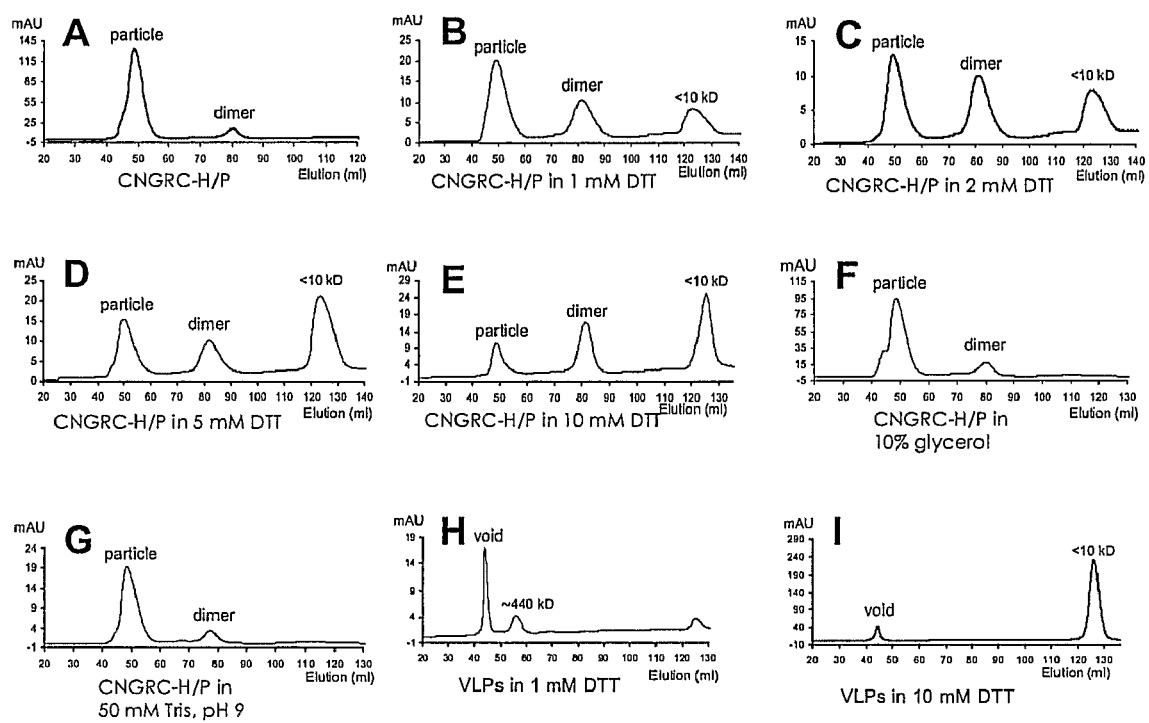
FIG. 8. The P-particle and VLP of VA387 were dissociated by dithiothreitol (DTT). A to E, chromatographs of the P-particle of the CNGRC—H/P mutant (A) treated by 1 mM (B), 2 mM (C), 5 mM (D), and 10 mM (E) DTT for 7 hours. The 3 peaks represent the P-particle, the P dimer, and the degraded products (<10 kDa), respectively. F and G, the same P-particles were treated with 10% glycerol (F) or 50 mM Tris, pH 9 (G). H and I, the VLP of VA387 was treated by 1 mM (H) or 10 mM (I) DTT.

To investigate if disulfide bridges play a role in promoting the P-particle formation, the cysteine-promoted P-particle was treated by dithiothreitol (DTT). The P-particle was sensitive to DTT treatment at a low concentration of 1 to 2 mM (FIG. 8A to C), indicating an intermolecular disulfide bond is indeed involved in the formation of the P-particle. However, further increasing DTT concentration (5 mM and 10 mM) did not lead to complete dissociation of the P-particle (FIGS. 8D and E), suggesting that some force other than disulfide bond may also involved in the P-particle formation. The disulfide bond may also be involved in the P dimer formation, because treatment of the P-particle with DTT resulted in degradation of the P dimer in a dose dependent manner (FIG. 8A to E). Furthermore, the disulfide bond might play a role in the capsid assembly, because a treatment of DTT lead to dissociation of VLPs in a dose-response manner (FIGS. 8H and I). In contrast, treatment of 10% glycerol or 50 mM Tris at pH 9 did not result in degradation of the P-particle (FIGS. 8F and G).

Figure 2:
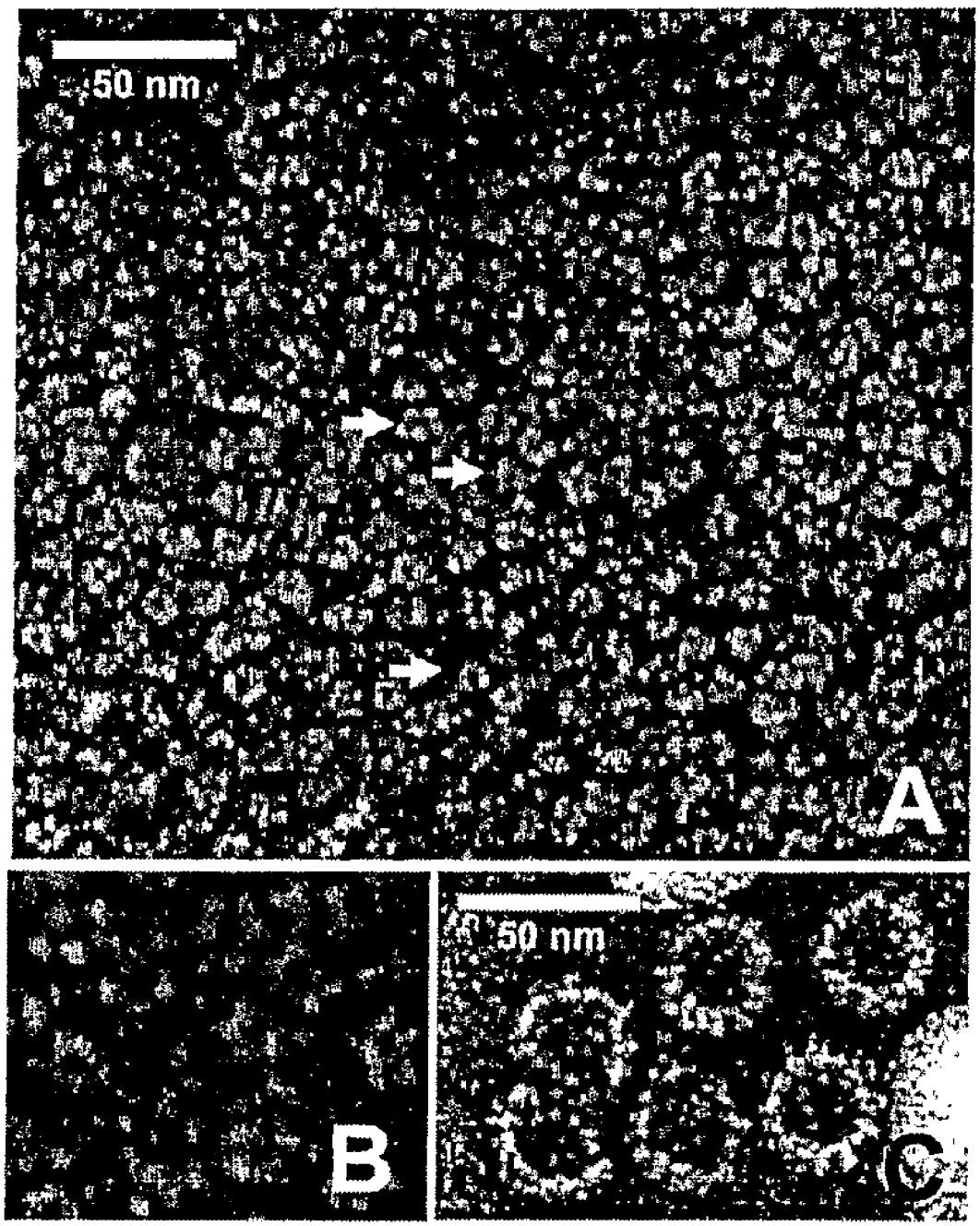
FIG. 2. Electron micrographs of the negatively stained P-particle. A and B, FPLC purified P-particle of the CNGRC-H/P mutant of VA387. Arrows indicate a few typical ring-shaped structures. One of them is enlarged in B. C, sucrose gradient-purified VA387 VLPs are shown at the same magnification. Bar=50 nm.

The P-particle revealed unique morphology under electron microscopy. We examined the FPLC-purified P-particle from different sources by a negative staining electron microscopy. As shown in FIG. 2, the P-particles of different sources revealed the same typical ring-shape structure in a diameter of ~5 nm, indicating that the P-particle is a spherical complex. This structure is specific for the P-particle, because the P protein from the dimer fractions did not reveal such a structure.

Figure 9:
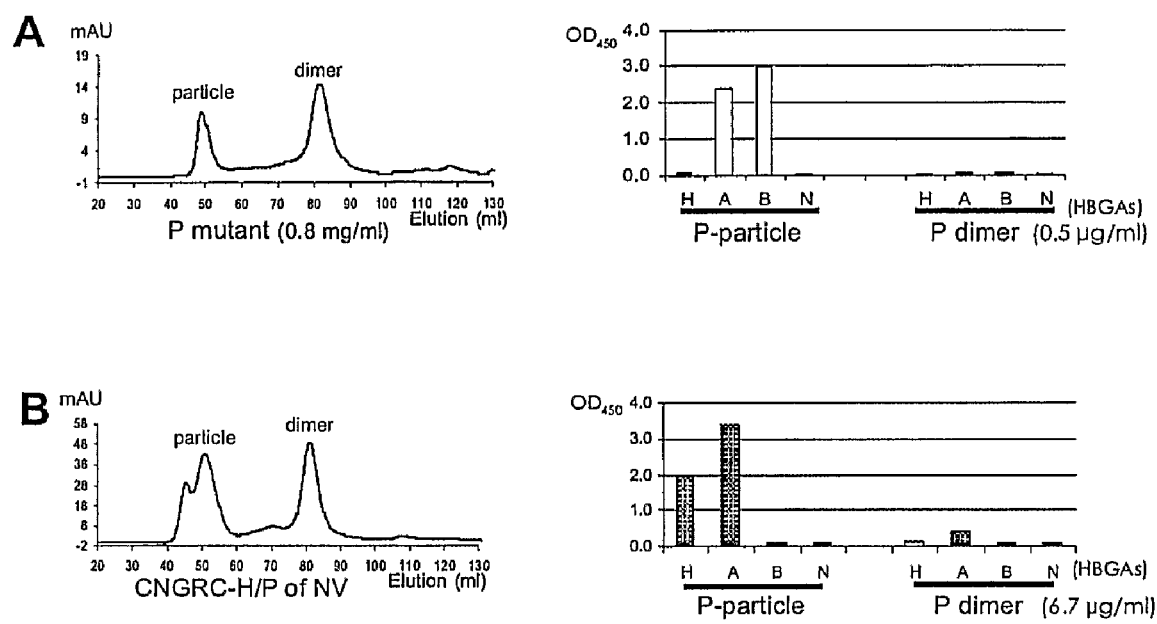
FIG. 9. The P-particle displays enhanced binding to HBGAs. A and B, Chromatographs of gel filtrations showing two peaks representing the P-particle and the P dimer, respectively, of the P mutant of VA387 (A, left panel) and the CNGRC-H/P mutant of NV (B, left panel). The two peak fractions were measured for their binding to HBGAs (right panel).

The P-particle displays enhanced binding ability to HBGA receptors. It has previously been demonstrated that the P dimers bind to HBGAs; however, the binding affinity is typically lower than that of the intact capsid. Further, the binding affinity of the P dimers is typically variable among the different P proteins studied. Since it is now known that varied P proteins differ in their ability to form the P-particle, it was hypothesized that the forms of the capsid proteins may be a factor affecting the binding affinities. A direct comparison of binding affinity between P dimer and complex confirmed our hypothesis: both VA387 and NV P-particles revealed significantly higher binding activities than that of the P dimers using both saliva and synthetic HBGAs (FIGS. 9A and B, data not shown).

To further determine the role of the P-particle formation in receptor binding, we performed a systematic comparison of receptor binding for all mutants we have generated (Table 2). In general, the ability to form the P-particle is correlated with the binding capability. The estimated binding sensitivities of VA387 P-particles to the B antigen were ~725-fold higher than that of the P dimers (Compare the H/P mutant to the CNGRC-H/P mutant in Table 2). This increased binding sensitivity is comparable to that of the intact capsid. Similar enhancement of the receptor binding of the P-particle was also observed for the NV, although the binding capability increases were less (81-fold for the A antigen) than that of VA387. It is noted that the binding enhancement to the A and/or the B epitopes were significantly higher than that to the H epitope for both VA387 and NV (Table 2). The recently proposed model of norovirus-receptor interaction suggested that there are two binding sites within the binding interface of the capsid, each for interaction with the H and the A/B epitopes, respectively. The different enhancement on H and A/B antigens could be a consequence of different folding or conformation of the P proteins affecting on the H binding site negatively.

The icosahedral capsid shows higher binding capability than those dissociated intermediates. To test if different forms of wild type capsid proteins also possess different binding capability, we examined the capsid integrity in receptor binding by partial dissociation of VA387 VLPs with 50 mM Tris at pH 9. Two peaks resulted in the gel filtration: the higher molecular peak in the void volume represents the intact VLP (FIGS. 3A and B left panel), while the ~110 kDa intermediate might be the capsid protein dimer. HBGAs binding assays using the two peak fractions that were adjusted to the same concentrations showed that the binding sensitivity of the dimers was significantly lower (81-fold for B antigen) than that of the VLPs (FIG. 3B right panel). Similar results also were observed for NV VLPs (FIG. 3C), indicating that the icosahedral capsid shows higher binding ability than those dissociated intermediates. It was noted that when the VA387 VLP was treated by the same Tris buffer containing 30% sucrose, a dissociated intermediate of ~440 kDa was seen (FIG. 3D), which also revealed lower binding capability than VLP. This ~440 kDa intermediate might represent the pentamer of the capsid protein dimer as an intermediate in the assembly pathway. The same intermediate also occurred when the VLP was treated by 1 mM DTT (FIG. 8H).

Figure 10:
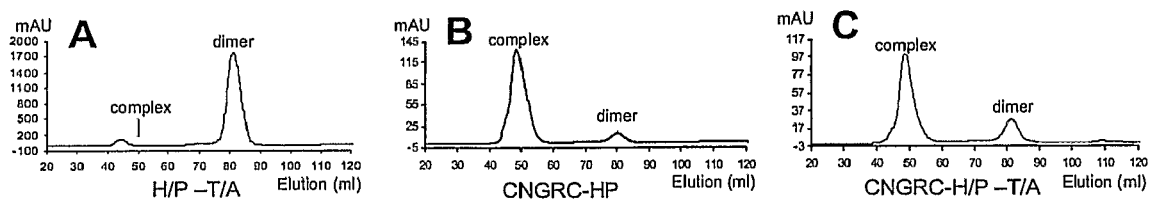
FIG. 10. The binding enhancement of the P-particle requires the authentic binding interface. A to C, gel filtration chromatographs of the mutants H/P-T/A (A), CNGRC-H/P (B), and CNGRC-H/P-T/A (C), indicating that the mutation T338A does not affect the P-particle formation of the CNGRC-H/P mutant. D and E, binding curves of H/P, CNGRC-H/P, CNGRCH/P-T/A, and CNGRC-MBP to saliva of 0, A, B and nonsecretor blood types (D) or to synthetic A- and B-trisaccharide-BSA conjugate (E). The data for binding curves are mean values of triplicates.
Figure 10:
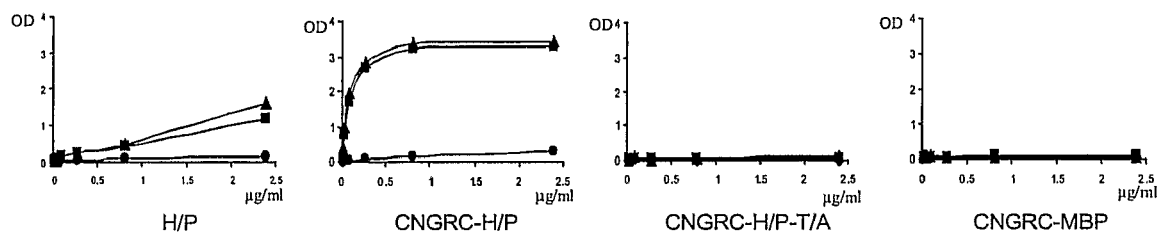
Figure 10:
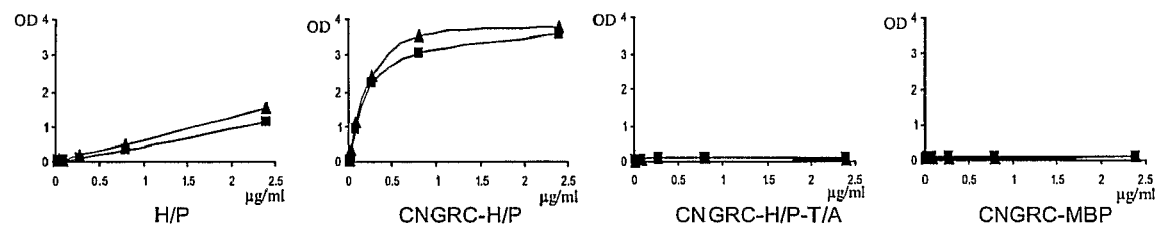

The binding enhancement requires the authentic binding interface. To further determine the role of the receptor-binding interface in the binding enhancement of the P-particle, we tested an H/P mutant of VA387 whose binding ability was destroyed by a single amino acid mutation at the threonine 338 ($T_{338}A$, H/P-T/A mutant). Addition of the short peptide CNGRC to the H/P-T/A mutant resulted in the P-particle formation (FIG. 10A, B and C) but did not result in binding to any of the A, B and H antigens (FIGS. 10D and E). This result indicates that the authentic binding interface is required for the binding enhancement of the P-particle.

Figure 4:
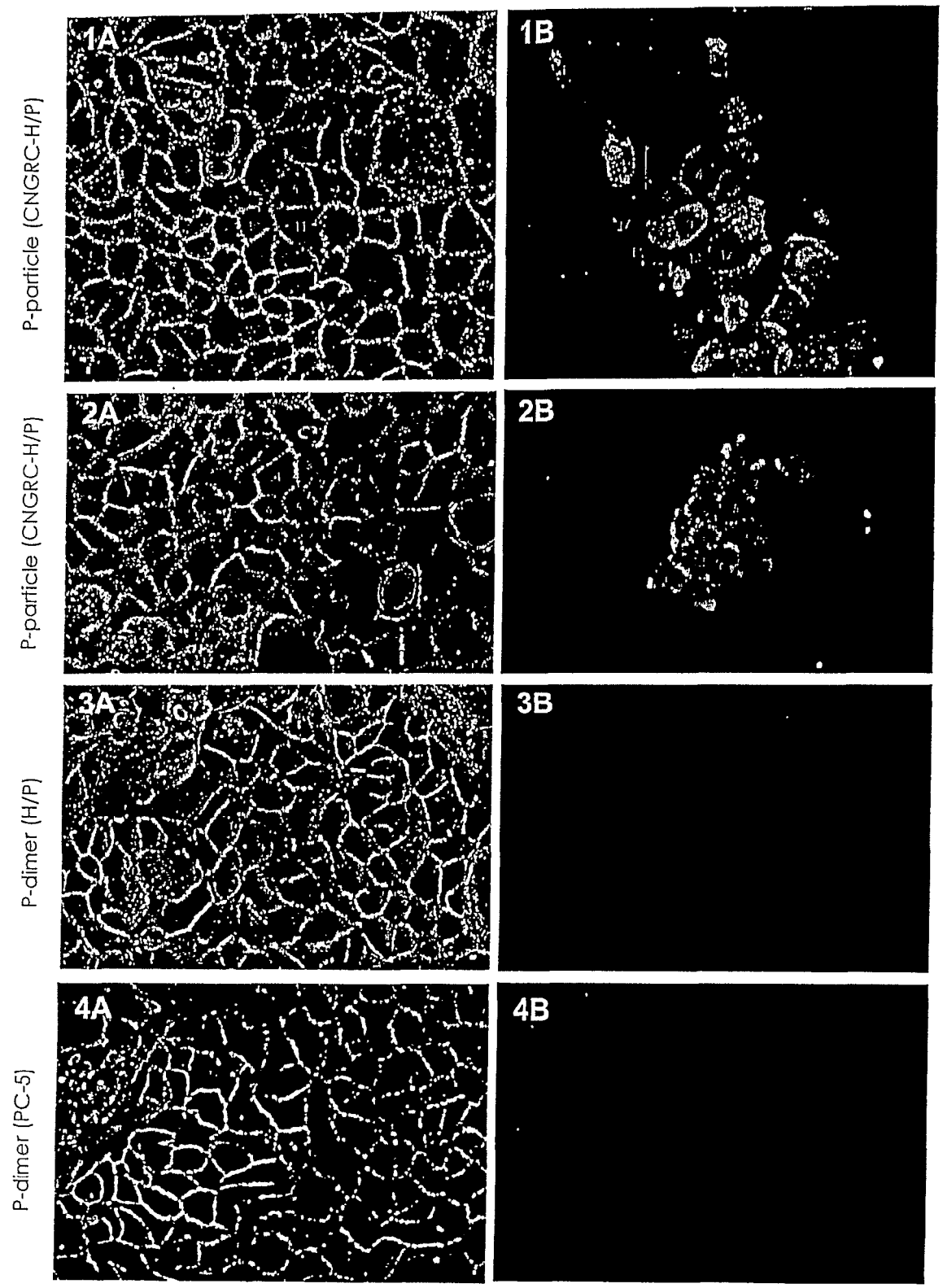
FIG. 4. The P-particle of VA387 binds to human enterocyte Caco-2 cells. The left panels are phase contrast micrographs of Caco-2 cells after incubating with the biotinylated P-particles (CNGRC-H/P) and P dimers (H/P and PC-5). The cell-bound P proteins were detected using FITC-Striptavidin (Pierce) observed by a fluorescence microscopy (right panels). Cells were 7 days after confluency. Micrographs in both panels show the same fields of the cell cultures.

The P-particle binds to human enterocyte Caco-2. To examine if the P-particle has a enhanced binding to human enterocyte, the Caco-2 cells, a human intestinal carcinoma cell line that expresses H type 1 HBGA after differentiation (Marioneau et al., 2002), was tested. The biotin-labeled VA387 P-particle (CNGRC—HP) showed strong binding to some Caco-2 cells (FIG. 4, rows 1A to 2B), while the P dimer of H/P mutant revealed no detectable binding to the same cells (FIG. 4, rows 3A and 3B). Another P dimer (PC-5) that is incapable to bind HBGAs (unpublished data) also indicated a negative result (FIG. 4, rows 4A and 4B). The binding of the P-particle to Caco-2 cells was partially blocked by the same unlabeled P-particle (data not shown), indicating that the binding is specific. D4

The P-particle blocks the binding of VLPs to HBGAs. We finally tested if the P-particle shares the same binding specificity to the HBGAs as that of the intact VLPs by performing blocking assays between NV and VA387. A previously isolated monoclonal antibody (9C3) that reacts to NV VLP but not to VA387 enables this blocking assay. As shown in FIG. 5, 57% binding of NV VLP (0.5 ng/microliter) to the A antigen was blocked by the P-particle of VA387 at a concentration of 0.41 ng/microliter (FIG. 9A). The blockage of the P-particle at a lower concentration (<0.41 ng/microliter) on binding of NV VLP to A antigen showed typical dose dependent manner, while higher concentrations of the P-particle did not increase the blockage significantly. The P-particle of VA387 also blocked the binding of NV VLP to H antigen in a dose dependent manner. 37% of binding was blocked by the P-particle at 11.1 ng/microliter. As expected, the P dimer showed only weak or no blocking effects on binding of NV VLP at the same concentration range, most likely due to its low binding affinity to both A and H antigens (FIG. 5B). To our surprise, the wild type VLP of VA387 had only weak blocking effect on the binding of NV VLP to A or H antigen (not shown). This result implies that VA387 and NV may react to different epitopes or different portions of A and H antigens. Even more surprising was that VA387 VLP enhanced binding of NV VLP to the B antigen in a typical dose-dependent manner (not shown). This binding enhancement reached a plateau of 3.1-fold at 3.7 ng/microliter of VA387 VLPs. It remains unclear what causes this enhancement.

What is claimed is:

1. A composition for inducing an immune response in an individual against Norovirus, the composition comprising a therapeutic amount of a P-particle in a suitable sterile, non-toxic physiological medium, wherein the P-particle comprises Norovirus capsid P domain monomers selected from the group consisting of SEQ ID NO:2, a P protein, a P protein without a hinge, a P protein with a hinge and a cysteine linked to the end of a P1 subdomain of the P protein, and mixtures thereof.

2. The vaccine of claim 1, wherein the P-particle comprises capsid P domain monomers from the Norovirus strain VA387.

3. A method of inducing an immune response in an individual against Norovirus, the method comprising the step of orally or parenterally administering to an individual at least one immunologically effective dose of a composition comprising an isolated P-particle, the P-particle comprising a P protein from a Norovirus strain recombinantly expressed or synthesized from a cDNA comprising a fragment of the cDNA sequence of the capsid protein of the Norovirus strain, and a pharmaceutical carrier, wherein the dose is effective in inducing the immune response in the individual.

4. The method of claim 3, wherein the fragment is SEQ ID NO:2.

5. The method of claim 3, wherein the protein comprises a cysteine linked to the end of a P1 subdomain of the P protein, and wherein the isolated P-particle comprises a plurality of P-Particles which have been purified.

6. The method of claim 5, wherein the cysteine linked to the end of the P1 subdomain of the protein, results in the P-particle being more stable than the original P-particle without the cysteine linkage.

7. An isolated P-particle comprising capsid P domain monomers from a Norovirus strain.

8. The isolated P-particle of claim 7, wherein the isolated P-particle comprises a plurality of capsid P domain monomers, the capsid P domain monomers selected from the group consisting of P protein without a hinge, and P protein with a hinge and a cysteine linked to the end of a P1 subdomain of the P protein, and mixtures thereof.

9. The isolated P-particles of claim 8, wherein the P protein without a hinge further comprises a cysteine linked to the end of the P1 subdomain of the P protein.

10. The isolated P-particles of claim 9, wherein the a cysteine linked to the end of a P1 subdomain of the P protein, resulst in the P-particles being more stable than the original P-particles without the cysteine modification.

11. The isolated P-particle of claim 7, wherein the Norovirus strain is selected from the group consisting of NV, MOH, and VA 387.

12. The isolated P-particle of claim 7, wherein the Norovirus strain is selected from the group consisting of NV, MOH, Mexico, VA207, VA387, 02-1419, C59, VA115, Hawaii, Snow Mountain, Hillington, Toronto, Leeds, Amsterdam, Idaho Falls, Lordsdale, Grimsby, Southampton, Desert Shield, Birmingham, and White Rivercap.

13. The isolated P-particle of claim 7, wherein the P-particle is a purified recombinant P-particle in the shape of an icosahedron, the icosahedron comprised of 24 monomer units of SEQ ID NO:2.

14. The isolated P-particle of claim 7, wherein the P-particle comprises capsid P domain monomers from the Norovirus strain VA387.

15. The composition according to claim 1, wherein the P-particle has increased receptor binding activity with human histo-blood group antigens as compared to a P dimer particle.

16. The composition according to claim 1, wherein the P-particle comprises a dimer of the P protein.

17. The composition according to claim 2, wherein the P protein without a hinge further comprises a cysteine linked to the end of the P1 subdomain of the P protein.

18. The method according to claim 3, wherein the Norovirus strain is VA387.

* * * * *

UNITED STATES PATENT AND TRADEMARK OFFICE
CERTIFICATE OF CORRECTION

PATENT NO. : 8,277,819 B2
APPLICATION NO. : 11/917862
DATED : October 2, 2012
INVENTOR(S) : Xi Jiang et al.

It is certified that error appears in the above-identified patent and that said Letters Patent is hereby corrected as shown below:

In The Specification

Column 1, lines 14-20 (approx), read "This invention was made with Government support by the U.S. National Institutes of Health (National Institute of Allergy and Infectious Diseases, grant ROI AI37093-7, and National Institute of Child Health and Human Development, grant HD13021) and the Department of Defense (DoD grant PR033018). The government has certain rights in this invention." which should be deleted and replaced with "This invention was made with government support under R01 AI037093, AI055649, and HD013021 awarded by the National Institutes of Health and PR033018 awarded by the Department of Defense. The government has certain rights in the invention."

Signed and Sealed this
Third Day of February, 2015

Michelle K. Lee
*Deputy Director of the United States Patent and Trademark Office*

SEQUENCE LISTING

<160> NUMBER OF SEQ ID NOS: 2

<210> SEQ ID NO 1
<211> LENGTH: 1620
<212> TYPE: DNA
<213> ORGANISM: Norovirus Strain VA387

<400> SEQUENCE: 1

```
atgaagatgg cgtcgaatga cgccagccca tctgatgggt ccacagccaa cctcgtccca      60
gaggtcaaca atgaggttat ggctttggag cccgttgttg gtgccgctat tgcggcacct     120
gtggcgggcc aacaaaacgt aattgacccc tggattagga ataattttgt acaagcccct     180
ggtggagagt ttacagtatc ccctagaaac gctccaggtg agatactatg gagcgcgccc     240
ttgggccctg atttgaaccc ctacctttct catttggcca gaatgtacaa tggttatgca     300
ggtggttttg aagtgcaggt aatcctcgcg gggaacgcgt tcaccgccgg gaaagtcata     360
tttgcagcag tcccaccaaa ttttccaact gaaggcttga gcccagcca ggttactatg      420 ttcccccata taatagtaga tgttaggcaa ttggaacctg tgttgatccc cttacctgat     480
gttaggaata acttctatca ttacaatcaa tcaaatgatt ctaccattaa attgatagca     540
atgctgtata caccacttag ggctaataat gctggggatg atgtcttcac agtctcttgt     600
cgagtcctca cgaggccatc ccccgatttt gatttcatat tcttggtgcc acccacagtt     660
gaatcaagaa ctaaaccatt caccgtcccg atcttaactg ttgaggaaat gtccaactca     720
agattcccca ttcctttgga aaagttgtac acgggtccca gcagtgcttt tgttgtccaa     780
ccacaaaatg gcaggtgcac gactgatggc gtgctcttag gcactaccca gctgtctgct     840
gtcaatatct gcaccttcag aggggatgtc acccacattg caggcagtca tgactatata     900
atgaatttgg catctcaaaa ttggaacaat tatgacccaa cagaagaaat cccagcccct     960
ctgggaactc cagatttcgt gggaaagatc caaggcatgc tcacccaaac cacaagagag    1020
gatggctcga cccgcgccca caaagctaca gtgagcactg gaactgtcca cttcactcca    1080
aagttgggca gtgttcaata caccactgac acaaacaatg attttcaaac tggccaaaac    1140
```

-continued

```
acgaaattca ccccagtcgg cgtcatccag gatggtaata accaccaaaa tgaacccag      1200 caatgggtac tcccaaatta ctcaggtaga actggtcata atgtgcacct agctcctgcc      1260
gttgccccca ctttcccagg cgagcaactt ctcttcttta ggtccactat gcccgggtgt      1320
agcgggtatc ccaacatgaa tctccattgc ctactccccc aggaatgggt gcagcacttc      1380
taccaagaag cagctccagc acaatctgat gtggctctgc tgagatttgt gaatccagac      1440
acaggtaggg ttctgtttga gtgcaagctc cataaatcag gctatgtcac agtggctcac      1500
actggcccgc atgatttggt tatcccccc aatggttatt ttagatttga ttcctgggtc       1560
aaccagttct acacacttgc ccccatggga atggagcgg ggcgcagacg tgcattataa       1620

<210> SEQ ID NO 2
<211> LENGTH: 957
<212> TYPE: DNA
<213> ORGANISM: Norovirus Strain VA387

<400> SEQUENCE: 2
tcaagaacta aaccattcac cgtcccgatc ttaactgttg aggaaatgtc caactcaaga        60
ttccccattc ctttggaaaa gttgtacacg ggtcccagca gtgcttttgt tgtccaacca       120
caaaatggca ggtgcacgac tgatggcgtg ctcttaggca ctacccagct gtctgctgtc       180
aatatctgca ccttcagagg ggatgtcacc cacattgcag gcagtcatga ctatataatg       240
aatttggcat ctcaaaattg gaacaattat gacccaacag aagaaatccc agcccctctg       300
ggaactccag atttcgtggg aaagatccaa ggcatgctca cccaaccac aagagaggat        360 ggctcgaccc gcgcccacaa agctacagtg agcactggaa ctgtccactt cactccaaag       420
ttgggcagtg ttcaatacac cactgacaca aacaatgatt ttcaaactgg ccaaaacacg       480
aaattcaccc cagtcggcgt catccaggat ggtaataacc accaaaatga accccagcaa       540
tgggtactcc caaattactc aggtagaact ggtcataatg tgcacctagc tcctgccgtt       600
gcccccactt tcccaggcga gcaacttctc ttctttaggt ccactatgcc cgggtgtagc       660
gggtatccca acatgaatct ccattgccta ctccccagg aatgggtgca gcacttctac        720
caagaagcag ctccagcaca atctgatgtg gctctgctga gatttgtgaa tccagacaca       780
ggtagggttc tgtttgagtg caagctccat aaatcaggct atgtcacagt ggctcacact       840
ggcccgcatg atttggttat ccccccaat ggttatttta gatttgattc ctgggtcaac       900
cagttctaca cacttgcccc catgggaaat ggagcgggc gcagacgtgc attataa          957
```